(12) United States Patent
Kuo et al.

(10) Patent No.: US 11,178,895 B2
(45) Date of Patent: Nov. 23, 2021

(54) COMPOSITION FOR ENHANCING IMMUNITY OF INSECTS AND METHOD THEREOF

(71) Applicant: NatureWise Biotech & Medicals Corporation, Taipei (TW)

(72) Inventors: Yu-Cheng Kuo, Taipei (TW); Chung-Yang Huang, Taipei (TW); Chia-Chung Hou, Taipei (TW); Chi-Jung Chen, Taipei (TW)

(73) Assignee: NATUREWISE BIOTECH & MEDICALS CORPORATION, Taipei (TW)

( * ) Notice: Subject to any disclaimer, the term of this patent is extended or adjusted under 35 U.S.C. 154(b) by 587 days.

(21) Appl. No.: 16/104,499

(22) Filed: Aug. 17, 2018

(65) Prior Publication Data

US 2019/0053526 A1 Feb. 21, 2019

(30) Foreign Application Priority Data

Aug. 18, 2017 (TW) .................................. 106128193

(51) Int. Cl.
| | | |
|---|---|---|
| *A23L 33/105* | (2016.01) | |
| *A61K 36/47* | (2006.01) | |
| *A61P 37/02* | (2006.01) | |
| *A23K 10/30* | (2016.01) | |
| *A23K 20/10* | (2016.01) | |
| *A61K 8/49* | (2006.01) | |
| *A61K 36/185* | (2006.01) | |

(52) U.S. Cl.
CPC ............ *A23L 33/105* (2016.08); *A23K 10/30* (2016.05); *A23K 20/10* (2016.05); *A61K 8/498* (2013.01); *A61K 36/47* (2013.01); *A61P 37/02* (2018.01); *A61K 36/185* (2013.01)

(58) Field of Classification Search
CPC .................................................... A23L 33/105
See application file for complete search history.

(56) References Cited

U.S. PATENT DOCUMENTS

| | | | | |
|---|---|---|---|---|
| 6,096,350 | A * | 8/2000 | Kemp ................... | A01N 59/00 424/661 |
| 9,932,579 | B2 * | 4/2018 | Paldi ...................... | A61K 31/00 |
| 9,993,492 | B2 * | 6/2018 | Schuhly ............... | A23K 20/158 |
| 2011/0171324 | A1 * | 7/2011 | Clemente ............... | A61K 33/34 424/680 |
| 2014/0220150 | A1 * | 8/2014 | Stamets ................ | A01N 65/00 424/537 |

FOREIGN PATENT DOCUMENTS

| | | |
|---|---|---|
| EP | 2 251 023 A1 | 11/2010 |
| EP | 3 443 974 A1 | 2/2019 |
| WO | WO 2014/060803 A1 | 4/2014 |

OTHER PUBLICATIONS

Ghosh et al., "Nutritional evaluation of four commercially available pollen patties in Korea", J Agriculture 2015 30 (3) 155-160.*
Bernays, "Evolution of feeding behavior in insect herbivores", BioScience, Jan. 1998, vol. 48, No. 1, pp. 35-44.*
Extended European Search Report dated Jan. 18, 2019, for European Application No. 18187461.1.
Heil et al., "Protective Ant-plant Interactions as Modes Systems in Ecological and Evolutionary Research", Annu. Rev. Evol. Syst., Nov. 2003, vol. 34, No. 1, pp. 425-453.
Kumazawa et al. "Analysis of antioxicant prenylflavonoids in different parts of Macaranga tanarius, the plant origin of Okinawan propolis" Asian Pacific Journal of Tropical Medicine, Jan. 20, 2014, pp. 16-20.
Mamase, "Trees and plants for bees and beekeepers in the Upper Mara Basin", Dec. 1, 2017, pp. 1-52.
Tseng et al., "Allelopathic Potential of *Macaranga tanarius* (L.) Muell.-ARG." Journal of Chemical Ecology, vol. 29, No. 5, May 2003, pp. 1269-1286.

* cited by examiner

*Primary Examiner* — Gina C Justice
(74) *Attorney, Agent, or Firm* — Birch, Stewart, Kolasch & Birch, LLP

(57) ABSTRACT

Provided is a use of a *Macaranga tanarius* preparation or extract for manufacturing a composition for enhancing immunity of an insect, particularly a bee. Also provided is a method for enhancing immunity of an insect, particularly a bee. The method comprises administering an effective amount of a composition of the present invention to the insect.

3 Claims, 6 Drawing Sheets

COMPOSITION FOR ENHANCING IMMUNITY OF INSECTS AND METHOD THEREOF

BACKGROUND OF THE INVENTION

Field of the Invention

The present invention relates to a composition for enhancing immunity of an insect, particularly a bee, and a method thereof.

Description of the Prior Art

The bee is one of the most contributing insects to the human and, in addition to the production of various by-products with health value, is also an important crop pollinator in agriculture. Therefore, if the bees' immunity can be improved to increase the survival rate (or prevent the death) of the reared bees, it will be extremely helpful to the related industries.

SUMMARY OF THE INVENTION

In one aspect, the present invention provides a use of a *Macaranga tanarius* preparation or extract for manufacturing a composition for enhancing immunity of an insect.

In another aspect, the present invention provides a method for enhancing immunity of an insect, comprising administering an effective amount of the composition described above to the insect.

In yet another aspect, the present invention provides a composition that can serve as a feed or a nutraceutical for enhancing immunity of an insect and comprise a *Macaranga tanarius* preparation or extract.

In a further aspect, the present invention provides a method for preventing an insect from disease or death, comprising administering an effective amount of the composition described above to the insect.

It is to be understood that both the foregoing general description and the following embodiments are exemplary and illustrative only, and are not intended to limit the present invention.

BRIEF DESCRIPTION OF THE DRAWINGS

The foregoing summary, as well as the following detailed description of the invention, will be better understood when read in conjunction with the appended figures. In the figures.

DETAILED DESCRIPTION OF THE EMBODIMENTS

Figure 1:
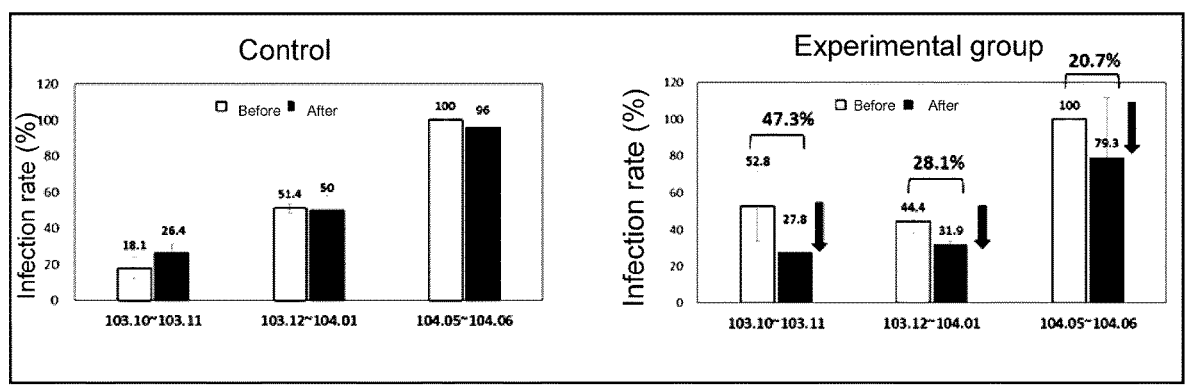
FIG. 1 shows that the composition of the present invention can decrease bee CBPV infection rate effectively.

In one aspect, the present invention provides a use of a *Macaranga tanarius* preparation or extract for manufacturing a composition for enhancing immunity of an insect.

In another aspect, the present invention provides a method for enhancing immunity of an insect, comprising administering an effective amount of the composition described above to the insect.

In yet another aspect, the present invention provides a composition that can serve as a feed or a nutraceutical for enhancing immunity of an insect and comprises a *Macaranga tanarius* preparation or extract.

In a further aspect, the present invention provides a method for preventing an insect from disease or death, comprising administering an effective amount of the composition described above to the insect.

According to the present invention, the composition can be prepared using any conventional method or standard process. In some embodiments of the present invention, the *Macaranga tanarius* extract is prepared by a method comprising the steps of: extracting dried *Macaranga tanarius* (preferably leaves and/or stamens) with a medium-high-polarity solvent to obtain a first extract; and removing the insoluble in the first extract to obtain the *Macaranga tanarius* extract. According to an embodiment of the present invention, the dried *Macaranga tanarius* leaves are extracted with a medium-high-polarity solvent (e.g., alcohol or acetone). The extract is concentrated and then mixed with an adsorbent resin, followed by sequential elution using solvents with decreasing polarity (e.g., water→methanol→acetone) to remove the insoluble. The extracts are combined and concentrated to obtain the *Macaranga tanarius* extract.

In other embodiments, the *Macaranga tanarius* preparation is prepared by grinding the dried *Macaranga tanarius* (preferably leaves and/or stamens thereof) into powder.

According to an embodiment of the present invention, the composition of the present invention is particularly effective for enhancing insect immunity of an insect, particularly a bee.

Since bees are on the verge of extinction, the present invention also provides a composition that can serve as a feed or a nutraceutical for enhancing immunity of bees and comprises a *Macaranga tanarius* extract.

EXAMPLES

Example 1

Preparation of the Composition of the Present Invention

Grinding Dried *Macaranga tanarius* Leaves Into Powder to Obtain Composition 1

The dried *Macaranga tanarius* leaves are extracted with a medium-high-polarity solvent (e.g., alcohol or acetone). The extract is concentrated and then mixed with an adsorbent resin, followed by sequential elution using solvents with decreasing polarity (e.g., water→methanol→acetone) to remove the insoluble. The extracts are combined and concentrated to obtain the *Macaranga tanarius* extract, which comprises 20 to 25% of tannin ingredients (including galloylglucoses, galloylshikimic acids, galloylquinic acids, corilagin, punicafolin, furosin, terchebin, geraniin, etc.) and 20-25% of flavonoid ingredients (including propolin C propolin D propolin F propolin G, etc.). The *Macaranga tanarius* extract can be used directly after drying or used after further granulation (for use as composition 2 or for preparation of composition 2).

Example 2

Disease Resistance of Bees Improved by the Composition of the Present Invention

A. Field Trials:

The experiment was carried out using a weak beehive group and a strong beehive group. Each group was composed of six beehives selected by the beekeepers, each beehive having close bee potential. The experimental group and the control group each had three beehives. The selection condition for the weak beehive group was the beehive with a small number of worker bees and a reduced spawning capacity of the queen bee. The selection criteria for the strong beehive group were the sister beehives gave birth by the same queen bee and having strong bee potential. Nutritional supplements used the pollen cake as the carrier. The beehives of the experimental group were provided with special pollen cakes containing Composition 1, and the control beehives were provided with common pollen cakes. After feeding continuously for one month, 24 bees inside the beehives were randomly sampled from each beehive to detect the differences in infection rates of Chronic Bee Paralysis Virus (CBPV).

1. Variation in Bee CBPV Infection Rate

Genomic RNA was extracted from the separated midgut of sampled worker bees from each group and CBPV infection condition of the bees was detected by Q-PCR. The variations in CBPV infection rates of the weak and strong beehive groups were observed, respectively. After one month of feeding the special pollen cake, the CBPV infection rate of the weak beehive treatment group decreased from 52.8±19.2% before feeding to 27.8±14.7%, in which two beehives had more than 60% reduction rate in CBPV. In the strong beehive group, the mean CBPV infection rate of the beehives of the treatment group was significantly decreased from 44.4±6.4% to 31.9±2.4% after one month of feeding the special pollen cake, which was still significantly lower than the mean infection rate of 50±8.3% in the control group. CBPV is a virus that is commonly infected in bee farms. The test results confirmed that the bee colonies that ate the pollen cake containing composition 1 could significantly reduce the infection rate of CBPV regardless of the strength of the bee potentials (see FIG. 1).

2. Detection of Immune Gene Expression Level in Bees

Figure 2:
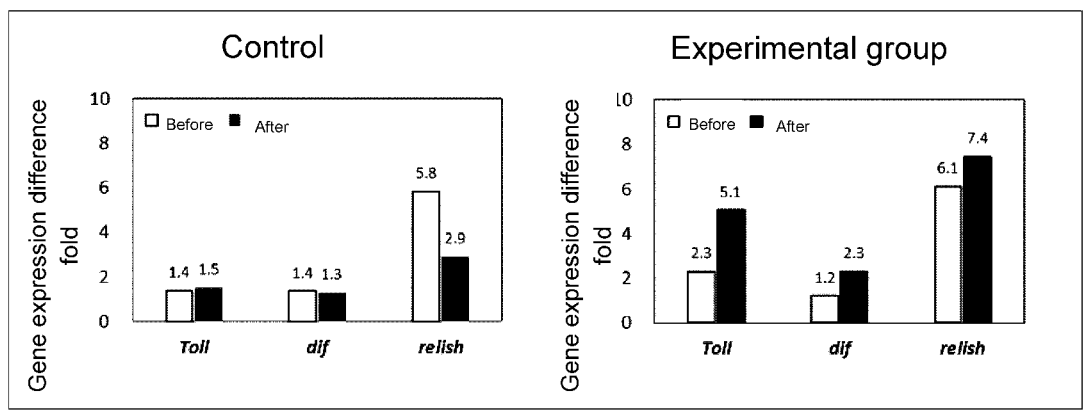
FIG. 2 shows that the composition of the present invention can decrease bee CBPV infection rate by inducing the immune mechanism of bees.

The genomics study found that insects have four immune signal pathways, including Toll, Imd, JAK/STAT and JNK. In this experiment, we selected the most studied Toll pathway-associated immune genes as targets, and detected the expression level of immune genes, such as toll, dif, relish, etc. in genomic RNA of sampled worker bees from each group. The experimental results showed that the expression levels of immune genes, such as toll and dif, in the bees of the control group were almost unchanged, while the toll gene expression level in the bees of the experimental group was increased by 1.89 to 2.51 times (see FIG. 2). It was confirmed that composition 1 can reduce CBPV infection by inducing the immune mechanism of bees.

B. Laboratory Test

To further confirm the results of the field trials, we took the honeycomb back from the apiary to hatch the newborn bees. Each test used 3-day-old newborn bees that emerged on the same day. The sugar water was used as the carrier. Different concentrations of *Macaranga tanarius* extracts as described in Example 1 were respectively formulated in 50% (w/v) sucrose water (Composition 2). For ten test bees in each group, the bees were placed in a 250 mL pudding cup and reared at room temperature (at a temperature of 26 to 30° C. and a humidity of 50 to 60%), and 1 mL of sugar water was provided daily for bees to freely feed.

1. Impact on the Survival Rate of Bees

Figure 3:
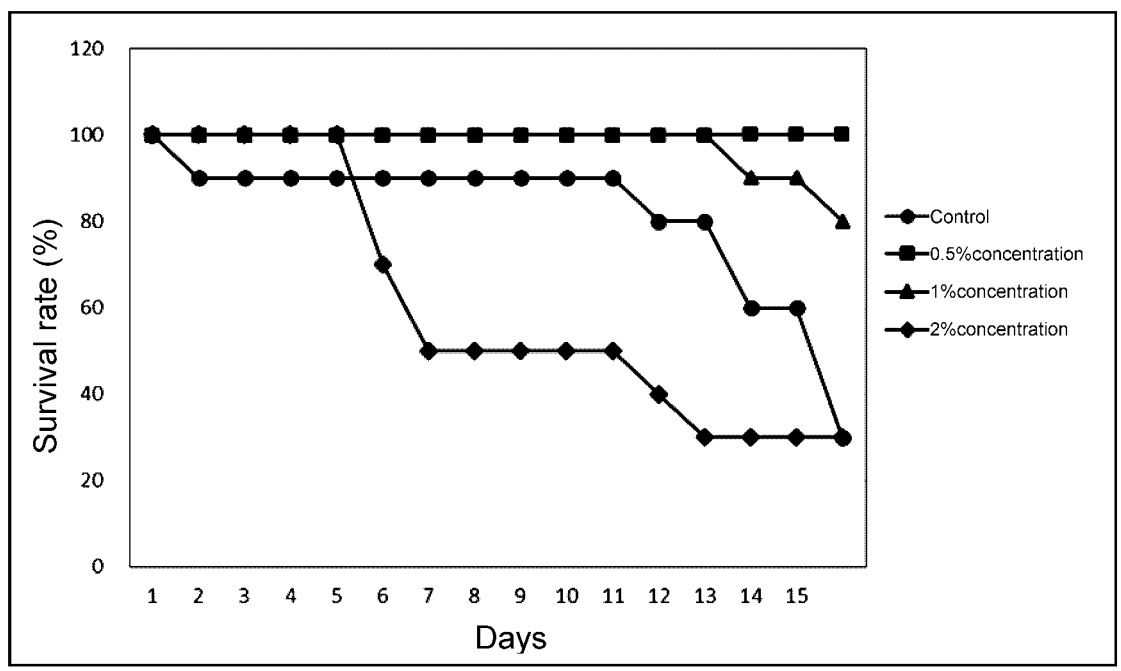
FIG. 3 shows that the composition of the present invention can extend the life span of bees.

Three concentrations (2 mg/mL, 1 mg/mL, 0.5 mg/ml) of *Macaranga tanarius* extracts were formulated in 50% sucrose water respectively, and the control group was given 50% sucrose water. The experimental results showed that on the 16th day, the survival rate of each group was 30% for the control group, 30% for the 2 mg/mL group, 80% for the 1 mg/mL group, and 100% for the 0.5 mg/mL group. The results showed that the survival rate of bees, which grew in an adversity environment, where the temperature, humidity, and volume are not suitable for bee growth, and fed with the composition 2 containing a concentration of 0.5 mg/mL *Macaranga tanarius* extract, can be significantly increased (see FIG. 3).

2. Influence on Expression Level of Bees' Immune Gene and CBPV

Figure 4:
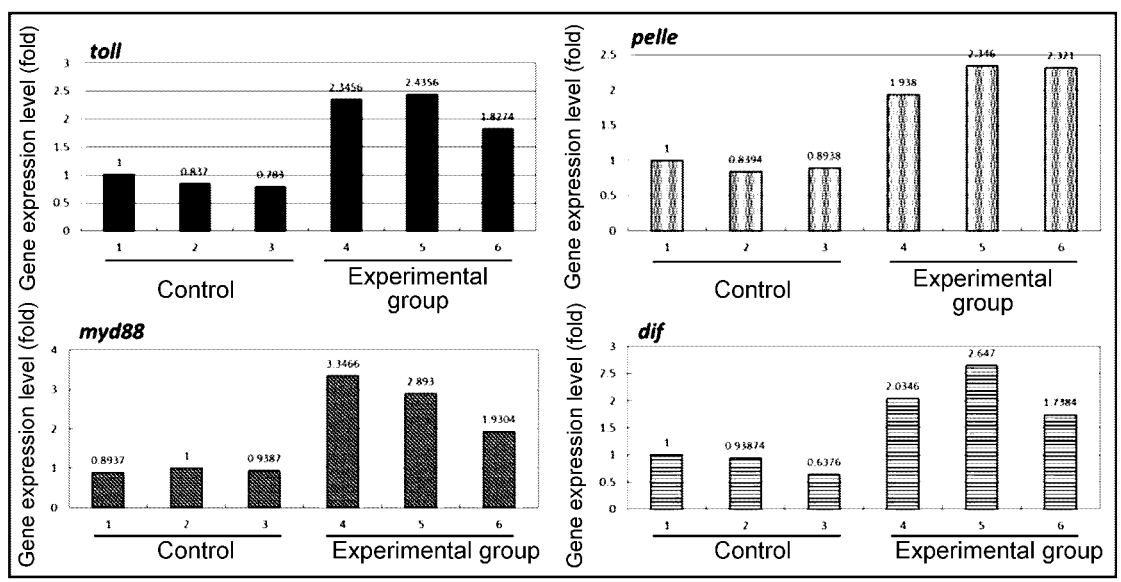
FIG. 4 shows that the composition of the present invention can improve immunity by induction of immune gene expression in individuals, which further inhibits hyperplasia of CBPV.

Three survival bees from the above control group and three survival bees from the above 0.5 mg/mL experimental group were tested for CBPV and expression level of immune genes, such as toll, dif, pelle and myd88. The experimental results are shown in FIG. 4. For bees fed with 0.5 mg/mL dietary supplements, the expression levels of toll, dif, pelle and myd88 genes were 2-3 times higher than those of the bees in control group (in average, 2.53 times increase in toll expression level, 2.89 times increase in myd88 expression level, 2.42 times increase in pelle expression level, and 2.48 times increase in dif expression level). The results of CBPV detection showed that two of the three worker bees in the control group had the original CBPV, whereas no CBPV was detected in the bees of experimental group. Based on the above results, it was confirmed that the enhancement of the immune gene expression level of the bees in the experimental group was not induced by the pathogenic stimulus, but was the result induced by feeding composition 2. CBPV can be infected vertically to the next generation via the queen bees. Newborn bees that had emerged at the same time from the same nest had extremely different CBPV infection rates after different treatments for two weeks. It is assumed that the bees that ate sugar water containing the *Macaranga tanarius* extract can improve immunity by induction of immune gene expression in individuals, which further inhibits hyperplasia of CBPV.

Example 3

Efficacy of the Composition of the Present Invention on the Enhancement of the Pesticide Resistance of Bees Many reports confirm that neonicotinoids cause damage to the immune system of bees and many species (Mason et al., 2013). It is clear that damage to the immune system may be one of the important causes of bee killing by imidacloprid (a pesticide). According to the experimental results of the composition of the invention on the survival rate of bees and the regulation of immune genes, in this experiment, field bees that are easily exposed to pesticides are used as the test subjects, and sugar water containing a concentration of 0.5 mg/mL of *Macaranga tanarius* extract is fed to observe whether the tolerance of bees to imidacloprid can be enhanced.

The experiment employed Topical application method with reference to US EPAOCSPP 850.3020: Honey Bee Acute Contact Toxicity Test. Imidacloprid active pharmaceutical ingredient was dissolved and diluted in acetone, in which the test concentration used two semi-lethal doses (LD50) of 6.7 ng/µL and 23.8 ng/µL appeared within 24 hours with reference to Suchail et al.'s paper (2000). After the bees were frozen and fainted, 1 µg/bee of the imidacloprid solution was administered quantitatively to the prothorax tergum of the bee by a microapplicator. The solvent control group was administered with 1 µg/bee of acetone. Each group had 10 bees. After the administration of the drug, the bees were transferred to a constant-temperature growth box for breeding. The sugar water containing 0.5 mg/mL of *Macaranga tanarius* extract was provided to feed the bees in the experimental group, and the control group was fed with 50% sucrose water. The number of dead bees was observed after 24 hours, and the corrected formula of death rate was {1−(number of dead bees in treatment group/death in solvent control group)}*100%.

Figure 5:
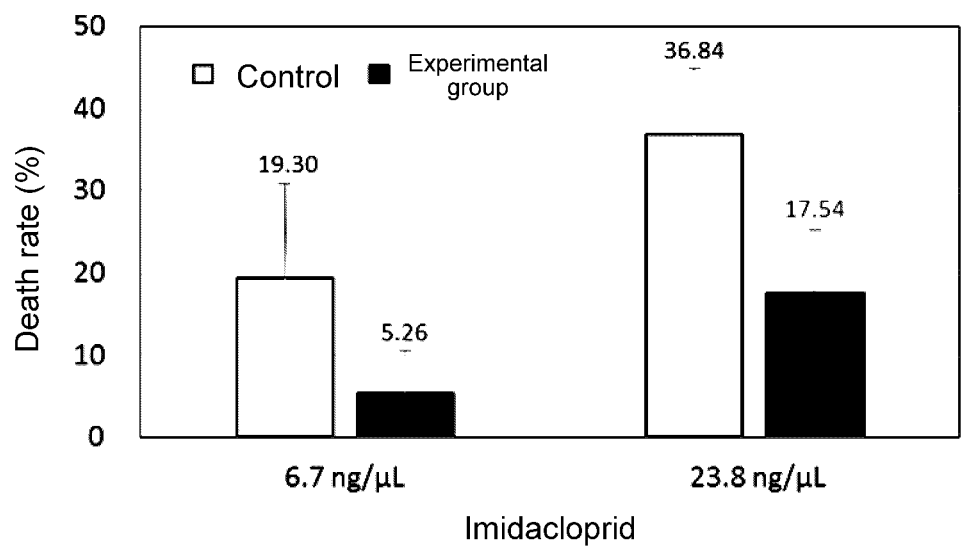
FIG. 5 shows that the composition of the present invention can improve the tolerance of bees to imidacloprid.

The experimental results showed that, in the 6.7 ng/µL imidacloprid treatment group, the 24-hour average mortality rate of bees eating sugar water containing *Macaranga tanarius* extract was 5.26%, which was significantly lower than that of the control group, i.e. 19.30%. For the 23.8 ng/µL imidacloprid treatment group, the 24-hour average mortality rate of bees eating sugar water containing *Macaranga tanarius* extract was 17.54%, which was also significantly lower than that of the control group, i.e. 36.84% (see FIG. 5), indicating that the edible composition 2 can improve the tolerance of bees to imidacloprid.

Example 4

Figure 6:
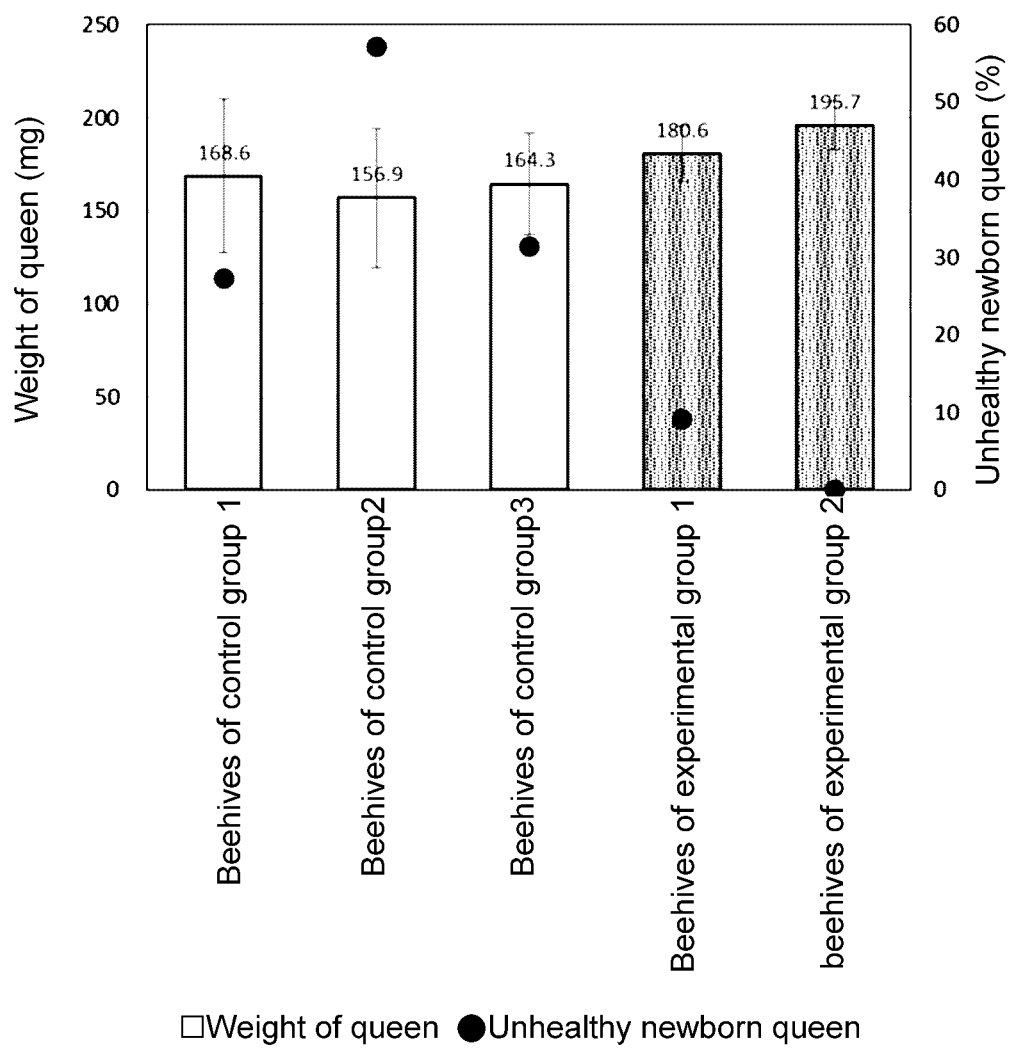
FIG. 6 shows that the composition of the present invention can increase the breeding rate of healthy queen bees.

The Increase of the Incubation Rate of Healthy Queen Bees by the Composition of the Present Invention In accordance with the practice of cooperating beekeepers in breeding queen bees, the queen bees were brought back to the laboratory for emerging at the age of 15 days to assess the weight and health of the newborn queen bees. The average weight of queen bees incubated in the control group was 163±34.4 mg, and the average weight of queen bees incubated in the experimental group was 178.1±25.4 mg. Statistical results showed no significant difference. At the same time, the proportion of unhealthy newborn queen bees in each group of emerged queen bees is assessed. The newborn queen bee having the symptoms, such as malformed wings, spat tongue, un-emergence, is considered unhealthy. The results showed that the proportion of unhealthy queen bees in the beehives of control group was 38.6%, while the proportion of unhealthy queen bees in the beehives of experimental group accounted for only 4.6% (see FIG. 6). Therefore, the composition of the present invention showed the effect of improving the production of healthy queen bees on the breeding of queen bees.

What is claimed is:

1. A method for enhancing immunity of a bee, comprising:
    administering an effective amount of a composition to the bee, wherein the composition comprises a *Macaranga tanarius* preparation or a *Macaranga tanarius* extract.

2. The method of claim 1, wherein the composition improves the survival rate of the bee.

3. A method for preventing a bee from an infection of Chronic Bee Paralysis Virus (CBPV), comprising:
    administering an effective amount of a composition to the bee, wherein the composition comprises *Macaranga tanarius* preparation or a *Macaranga tanarius* extract.

* * * * *